United States Patent [19]

Bright et al.

[11] Patent Number: 5,508,462

[45] Date of Patent: Apr. 16, 1996

[54] PROCESS FOR MAKING HYDROXY-TERMINATED AROMATIC OLIGOMERIC PHOSPHATES

[75] Inventors: Danielle A. Bright, New City; Ronald L. Pirrelli, Hartsdale, both of N.Y.

[73] Assignee: Akzo Nobel NV, Arnhem, Netherlands

[21] Appl. No.: 350,911

[22] Filed: Dec. 7, 1994

[51] Int. Cl.$^6$ .................................................. C07F 9/145
[52] U.S. Cl. .................................................. 558/99
[58] Field of Search .................................................. 558/99

[56] References Cited

U.S. PATENT DOCUMENTS

| | | | |
|---|---|---|---|
| 2,682,521 | 6/1954 | Coover, Jr. | 528/168 |
| 2,952,666 | 9/1960 | Coover, Jr. et al. | 528/72 |
| 3,965,220 | 6/1976 | Schumacher | 558/101 |
| 4,463,130 | 7/1984 | Serini et al. | 525/67 |
| 4,510,101 | 4/1985 | Pawloski et al. | 260/928 |
| 5,393,621 | 2/1995 | Chaloner-Gill | 429/192 |

FOREIGN PATENT DOCUMENTS

| | | | |
|---|---|---|---|
| 0509506 | 10/1992 | European Pat. Off. | C07F 9/12 |
| 0521628 | 1/1993 | European Pat. Off. | C07F 9/12 |
| 227632 | 9/1988 | Japan | C08G 79/04 |
| 223158 | 9/1989 | Japan | C08L 71/04 |
| 0064218 | 3/1978 | Romania . | |

OTHER PUBLICATIONS

*Chemical Abstracts*, vol. 92, No. 24140; Petreus et al. Ro–64218 (31 Mar. 1978).

*Primary Examiner*—Johann Richter
*Assistant Examiner*—Michael G. Ambrose
*Attorney, Agent, or Firm*—Richard P. Fennelly; Louis A. Morris

[57] ABSTRACT

The present invention is a process for forming hydroxy-terminated aromatic oligomeric phosphates by the initial reaction of a monoaryl dihalophosphate, such as monophenyl dichlorophosphate, with an aromatic diol, such as resorcinol, to form a halo-terminated aromatic oligomeric phosphate and the subsequent reaction of that halo-terminated phosphate with aromatic diol to form the hydroxy-terminated aromatic oligomeric phosphate. The initial and subsequent reactions preferably employ a Lewis acid catalyst, such as magnesium dichloride.

8 Claims, No Drawings

PROCESS FOR MAKING HYDROXY-TERMINATED AROMATIC OLIGOMERIC PHOSPHATES

BACKGROUND OF THE INVENTION

Aromatic oligomeric phosphate compositions which are not hydroxy-terminated are known to persons of ordinary skill in the art with representative examples being described in European Patent Publication Nos. 509,506 and 521,628 and Japanese Patent Publication No. 227,632/1988.

A hydroxy-terminated aromatic oligomeric phosphate is depicted as one of the products formed by the processes described in Japanese Patent Publication No. 223,158/1989. The product that is desired is a mixture of 22%–65%, by weight, of a reactive, hydroxy-terminated monophosphate ester, 15%–30% of a non-reactive, non-hydroxy-terminated phosphate ester, and 5%–63% of the hydroxy-terminated oligomeric phosphate ester. The process used to synthesize the product desired by the patentees of Japanese Patent Publication No. 223,158/1989 relies, for example, upon the reaction of a mixture of phenol and aromatic diol (e.g., resorcinol) with phosphorus oxychloride in the presence of a catalyst (e.g., aluminum chloride).

SUMMARY OF THE INVENTION

The present invention is a process for forming hydroxy-terminated aromatic oligomeric phosphates by the initial reaction of a monoaryl dihalophosphate, such as monophenyl dichlorophosphate, with an aromatic diol, such as resorcinol, to form a halo-terminated aromatic oligomeric phosphate and the subsequent reaction of that halo-terminated phosphate with aromatic diol to form the hydroxy-terminated aromatic oligomeric phosphate. The initial and subsequent reactions preferably employ a Lewis acid catalyst, such as magnesium dichloride.

DESCRIPTION OF PREFERRED EMBODIMENTS

The initial process step in the instant process for forming hydroxy-terminated aromatic oligomeric phosphates is the initial reaction of a monophenyl dihalophosphate with an aromatic diol to form a halo-terminated aromatic oligomeric phosphate. The monophenyl dihalophosphate is of the formula $ArOP(O)X_2$, where Ar stands for substituted or unsubstituted phenyl and X stands for halo, such as chloro or bromo. A preferred reagent to use is monophenyl dichlorophosphate. The aromatic diol is of the formula HOROH, with R being a hydrocarbyl group such as phenyl, diphenyl, 4,4'-isopropylidenediphenyl, and the like. A particularly preferred diol is resorcinol. Others which can be used include hydroquinone, bisphenol A, bisphenol S, and 4,4-diphenol. This initial reaction step is preferably conducted at an elevated temperature of about 50° C. to about 130° C. using an effective amount (about 0.1% to about 0.5%, by weight of the dihalophosphate) of a Lewis acid catalyst, such as magnesium dichloride. The resulting halo-terminated product from this reaction is an aromatic oligomeric phosphate of the following formula:

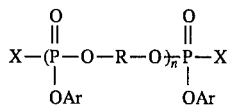

with Ar and X being defined as earlier described and n ranging from 1 to about 10. Mixtures where n is a decimal number are also contemplated.

This halo-terminated reaction product is then reacted with additional diol in a subsequent reaction step to substitute the halo-termination with the HO—R—O— group from the diol to yield the desired hydroxy-terminated aromatic oligomeric phosphate product:

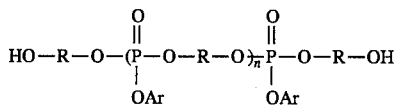

This second reaction step is also preferably conducted at an elevated temperature of about 110° C. to about 180° C.

The resulting product can be used as a reactive flame retardant in forming polycarbonate resin compositions. It can also be used as an additive flame retardant in polycarbonate resin compositions such as described and claimed in copending U.S. Ser. No. 350,601, filed on even date herewith.

The present invention is further illustrated by the Examples which follow.

EXAMPLE 1

To 1403 g (6.65 miles) of monophenyl dichlorophosphate was added 3.5 g of magnesium chloride and 366 g of resorcinol. The reaction mixture was heated with stirring to 110° C. over thirty minutes and kept at this temperature for an additional two hours. At the end of this time all the hydroxy groups were reacted. The reaction mixture was cooled to 50° C. and an additional 750 g (6.82 moles) of resorcinol was added to the reaction mixture. The temperature was increased to 110° C., and the mixture became dark purple. The temperature was gradually increased to 150° C. over six hours and was kept there for an additional two hours. At the end, the reaction mixture was orange. It was cooled to 70° C. and was washed twice with a 5% sodium carbonate solution and three times with water.

After removal of traces of water at 80° C. under vacuum, there was left 1380.5 g of an extremely viscous orange oil that did not flow at room temperature. The percent yield was 82%. The material had the following composition:

$P_1$—(OH)$_3$: 2%
$P_1$—(OH)$_2$: 22%
$P_2$—(OH)$_2$: 29%
$P_3$—(OH)$_2$: 14%
$P_4$—(OH)$_2$: 9%
$P_5$—(OH)$_2$: 5%
$P_6$—(OH)$_2$ to $P_{10}$(OH)$_2$: 5%

We claim:

1. A process for forming hydroxy-terminated aromatic oligomeric phosphates which comprises the initial reaction of a monoaryl dihalophosphate with an aromatic diol to form a halo-terminated aromatic oligomeric phosphate and the subsequent reaction of that halo-terminated phosphate with aromatic diol to form the hydroxy-terminated aromatic oligomeric phosphate.

2. A process as claimed in claim 1 wherein the monoaryl dihalophosphate is monophenyl dichlorophosphate.

3. The process as claimed in claim 1 wherein the aromatic diol is resorcinol.

4. The process as claimed in claim 1 wherein the monoaryl dihalophosphate is monophenyl dichlorophosphate and the aromatic diol is resorcinol.

5. The process as claimed in claim 1 wherein the initial and subsequent reactions employ a Lewis acid catalyst.

6. A process as claimed in claim 5 wherein the catalyst is magnesium dichloride.

7. The process as claimed in claim 5 wherein the monoaryl dihalophosphate is monophenyl dichlorophosphate and the aromatic diol is resorcinol.

8. A process as claimed in claim 5 wherein the catalyst is magnesium dichloride, the monoaryl dihalophosphate is monophenyl dichlorophosphate, and the aromatic diol is resorcinol.

* * * * *